(12) United States Patent
Brown

(10) Patent No.: US 9,119,707 B2
(45) Date of Patent: Sep. 1, 2015

(54) SENSORY MOTOR STIMULATION GARMENT AND METHOD

(75) Inventor: Timothy W. Brown, Newport Beach, CA (US)

(73) Assignee: INTELLISKIN USA, LLC, Newport Beach, CA (US)

( * ) Notice: Subject to any disclaimer, the term of this patent is extended or adjusted under 35 U.S.C. 154(b) by 33 days.

(21) Appl. No.: 12/551,420

(22) Filed: Aug. 31, 2009

(65) Prior Publication Data

US 2010/0010568 A1     Jan. 14, 2010

(51) Int. Cl.
  *A61F 5/37*   (2006.01)
  *A61F 5/02*   (2006.01)
  *A41D 13/00*  (2006.01)

(52) U.S. Cl.
  CPC ............ *A61F 5/026* (2013.01); *A41D 13/0015* (2013.01)

(58) Field of Classification Search
  CPC ............ A61F 5/026; A61F 5/02; A61F 5/37; A41D 3/0015
  USPC ................. 128/874, 875, 873, 869, 846, 845; 602/19, 60; 2/69, 44, 45
  See application file for complete search history.

(56) References Cited

U.S. PATENT DOCUMENTS

| | | | |
|---|---|---|---|
| 1,129,515 A | 2/1915 | Perry | |
| 2,477,792 A | 1/1947 | Fratianni | |
| 2,456,190 A | 12/1948 | Heilbronner | |
| 2,986,740 A | 6/1961 | Schudson | |
| 3,078,699 A | 2/1963 | Huntley | |
| 3,292,616 A | 12/1966 | Freeman | |
| 3,663,797 A | 5/1972 | Marsh | |
| 3,683,910 A | 8/1972 | Mckenna | |
| 4,325,379 A | 4/1982 | Ozbey | |
| 5,201,074 A | 4/1993 | Dicker | |
| 5,306,229 A | 4/1994 | Brandt et al. | |
| 5,328,447 A * | 7/1994 | Kapounek et al. | 602/19 |
| 5,344,384 A | 9/1994 | Ostrow et al. | |
| 5,367,708 A | 11/1994 | Fujimoto | |
| 5,555,566 A | 9/1996 | Kuhn | |

(Continued)

FOREIGN PATENT DOCUMENTS

| | | |
|---|---|---|
| DE | 202009013969 | 3/2010 |
| EP | 1891868 A1 | 2/2008 |

(Continued)

OTHER PUBLICATIONS

International Search Report and Written Opinion, PCT/US2010/045427, Nov. 25, 2010, 10 pgs.

(Continued)

*Primary Examiner* — Victoria J Hicks
(74) *Attorney, Agent, or Firm* — Morgan, Lewis & Bockius LLP

(57) ABSTRACT

A garment for stimulation of a wearer's sensory motor system. The garment includes a main body portion that includes an anterior portion and a posterior portion and at least one sensory motor stimulation member associated with the main body portion. The garment is configured to be worn over at least a portion of the wearer's torso and is form-fitting when worn by the wearer. The at least one sensory motor stimulation member contacts the wearer's skin when the garment is worn and is fabricated of an elastomeric material that causes the garment to stimulate the cutaneous nerve receptors in the wearer's skin contacted by the at least one sensory motor stimulation member.

18 Claims, 11 Drawing Sheets

(56) References Cited

U.S. PATENT DOCUMENTS

| | | | |
|---|---|---|---|
| 5,662,512 | A | 9/1997 | Cohen |
| 5,742,936 | A | 4/1998 | Tronc |
| 5,820,575 | A * | 10/1998 | Cabrera et al. ............... 602/19 |
| 5,823,851 | A | 10/1998 | Dicker |
| 5,857,990 | A | 1/1999 | Maas |
| 5,873,768 | A | 2/1999 | Fleishman-Ament et al. |
| 5,937,442 | A * | 8/1999 | Yamaguchi et al. ............. 2/69 |
| 6,176,816 | B1 | 1/2001 | Dicker et al. |
| 6,306,111 | B1 | 10/2001 | Dean |
| D457,709 | S | 5/2002 | Davis |
| 6,440,094 | B1 | 8/2002 | Maas |
| 6,464,656 | B1 | 10/2002 | Salvucci et al. |
| 6,936,021 | B1 | 8/2005 | Smith |
| 6,945,945 | B2 | 9/2005 | Givler et al. |
| 7,037,281 | B1 | 5/2006 | Jeffrey et al. |
| 7,037,284 | B2 | 5/2006 | Lee |
| 7,041,074 | B1 * | 5/2006 | Averianov et al. ............. 602/20 |
| D525,412 | S | 7/2006 | O'Mahony |
| 7,134,969 | B2 | 11/2006 | Citron et al. |
| 7,415,734 | B2 | 8/2008 | Donnelly |
| 7,516,498 | B2 | 4/2009 | Torry |
| 7,841,369 | B1 | 11/2010 | Osborne |
| D628,771 | S | 12/2010 | Kanada et al. |
| 7,861,319 | B2 | 1/2011 | Torry |
| 7,871,388 | B2 | 1/2011 | Brown |
| 2002/0143373 | A1 | 10/2002 | Courtnage et al. |
| 2005/0112976 | A1 | 5/2005 | McMurrey et al. |
| 2005/0197607 | A1* | 9/2005 | Brown ........................... 602/19 |
| 2005/0240134 | A1 | 10/2005 | Brown |
| 2008/0060113 | A1 | 3/2008 | Walsh |
| 2008/0194178 | A1 | 8/2008 | Smith |
| 2008/0208089 | A1* | 8/2008 | Newkirk et al. ............... 602/19 |
| 2008/0295230 | A1 | 12/2008 | Wright et al. .................. 2/455 |
| 2009/0062704 | A1 | 3/2009 | Brown et al. .................. 602/19 |
| 2009/0133181 | A1 | 5/2009 | Nordstrom et al. ............. 2/115 |
| 2009/0320180 | A1 | 12/2009 | Torry |
| 2010/0010568 | A1 | 1/2010 | Brown |
| 2010/0050313 | A1 | 3/2010 | Shackelford, Jr. |
| 2010/0242151 | A1 | 9/2010 | Mather |
| 2010/0256717 | A1 | 10/2010 | Brown |
| 2010/0299799 | A1 | 12/2010 | Belluye et al. |
| 2011/0131697 | A1 | 6/2011 | Kawahara |
| 2011/0213283 | A1 | 9/2011 | Brown |
| 2011/0271415 | A1 | 11/2011 | Torry |
| 2012/0078147 | A1 | 3/2012 | Ogulnick et al. |

FOREIGN PATENT DOCUMENTS

| | | |
|---|---|---|
| EP | 2505089 A2 | 10/2012 |
| JP | 2002-302810 | 10/2002 |
| JP | 2004-100116 | 4/2004 |
| JP | 2012-031564 A | 2/2012 |
| WO | WO 2005/086752 A2 | 9/2005 |
| WO | WO 2005/086840 A2 | 9/2005 |
| WO | WO 2008/002432 A2 | 1/2008 |
| WO | WO 2008/093105 A1 | 8/2008 |
| WO | WO 2011/025675 A1 | 3/2011 |
| WO | WO 2013/016670 A1 | 1/2013 |

OTHER PUBLICATIONS

Intelliskin USA LLC, Communication pursuant to Article 94(3) EPC, EP 10745106.4, Jan. 14, 2013, 5 pgs.
Brown, Office Action, U.S. Appl. No. 12/756,114, Dec. 19, 2012, 23 pgs.
Intelliskin LLC, ISR and Written Opinion, PCT/US2010/048648, Oct. 11, 2012, 10 pgs.
Brown, Interview Summary, U.S. Appl. No. 12/126,338, Jan. 31, 2014, 3 pgs.
Brown, Office Action, U.S. Appl. No. 13/559,507, Aug. 23, 2013, 13 pgs.
Brown, Office Action, U.S. Appl. No. 12/756,114, Jul. 18, 2013, 23 pgs.
Brown, Office Action, U.S. Appl. No. 12/126,338, Jun. 11, 2013, 17 pgs.
Brown, Final Office Action, U.S. Appl. No. 12/126,338, Feb. 15, 2011, 18 pgs.
Brown, Office Action, U.S. Appl. No. 12/126,338, Jun. 9, 2010, 14 pgs.
Brown, Office Action, U.S. Appl. No. 13/559,507, Dec. 17, 2013, 15 pgs.
Brown, Office Action, U.S. Appl. No. 13/831,228, Apr. 4, 2014, 5 pgs.
Intelliskin USA LLC, Communication under Rule 71(3) EPC Intention to Grant, EP 10745106.4, Oct. 17, 2013, 6 pgs.
Intelliskin USA LLC, International Preliminary Report on Patentability, PCT/US2010/048648, Jan. 28, 2014, 6 pgs.
Intelliskin USA LLC, Notification of the First Office Action, JP 2012-526827, Mar. 13, 2014, 4 pgs.
Brown, Final Office Action, U.S. Appl. No. 13/559,507, Jul. 11, 2014, 18 pgs.
Intelliskin USA LLC, Notification of the Office Action, JP 2013/017534, May 30, 2014, 4 pgs.
Intelliskin USA LLC, Notification of the Office Action, JP 2014/003694, Sep. 12, 2014, 3 pgs.
Intelliskin USA LLC, Decision to Grant, EP10745106.4, Oct. 2, 2014, 3 pgs.
Intelliskin USA LLC, Patent Examination Report, AU2010286851, Aug. 21, 2014, 3 pgs.
Brown, Final Office Action, U.S. Appl. No. 13/831,228, Feb. 13, 2015, 6 pgs.
Intelliskin USA LLC, International Search Report and Written Opinion, PCT/US2014/029690, Jul. 18, 2014, 9 pgs.
Intelliskin USA LLC, Decision to Grant, JP 2012-526827, Oct. 20, 2014, 5 pgs.
Intelliskin USA LLC, Certificate of Patent, JP 2012-526827, Dec. 10, 2014, 3 pgs.
Intelliskin USA LLC, Decision of Registration, JP2013-017534, Aug. 28, 2014, 2 pgs.
Intelliskin USA LLC, Certificate of Registration, JP2013-017534, Nov. 12, 2014, 3 pgs.
Intelliskin USA LLC, Certificate of Grant, EP10745106.4, Oct. 29, 2014, 3 pgs.
Intelliskin USA LLC, Notification of the First OA, CN201280046850.4, Dec. 24, 2014, 13 pgs.
Intelliskin USA LLC, Extended European Search Report, EP14188899.0, Mar. 11, 2015, 5 pgs.
Actively Yours. http://www.activelyyours.com/Merchant2/merchant.mvc?page=AY/PROD/cycling/Island_Jersey. Dec. 2010. ""HIND Island Cycling Jersey Short Sleeve"", 1 pg.
Brown, Final Office Action, U.S. Appl. No. 29/449,312, May 8, 2015, 7 pgs.
bizzieliving. http://www.bizzieliving.com/improve-your-posture-while-you-excercise/. Dec. 2011. Intelliskin Shirt, 3 pgs.
DHGate. http://www.dhgate.com/product!sports-compression-running-fitness-excercise/164726955.html. Date Unknown: Viewed May 2015. "sports compression running Fitness Excercise cycling short sleeve Clothing shirt", 11 pgs.
DailyStoke. http://www.dailystoke.com/gear-categories/intelliskin-gear-review-good-enuf-for-kelly-slater-good-enuf-for-you/. Nov. 29, 2011. "Intelliskin shirt", 4 pgs.
DailyPilot. http://!articles.dailypilot.com/2012-01-09/news/tn-dpt-0110-brown-20120109_1_bad-posture-perfect-posture-products. Jan. 2012, Intelliskin Shirt, 1 pg.
GearPatrol. http:l/gearpatrol.com/2011/07/07/intelliskin-foundation-shirt-2-0/. Jul. 7, 2011. "Intelliskin Foundation Shirt 2.0", 2 pgs.
News & Views. http:l/news.health.com/2011/05/24/can-toning-clothing-really-help-you-lose-weight/. May 2011, Intelliskin Eve Shirt, 1 pg.

\* cited by examiner

SENSORY MOTOR STIMULATION GARMENT AND METHOD

FIELD OF THE INVENTION

The present invention relates generally to body mechanics and, more particularly, to posture improvement garments configured to be worn on a user's upper body and that promote sensory motor system stimulation.

BACKGROUND OF THE INVENTION

The importance of good posture is well known among health professionals. Posture generally refers to the alignment of the body and, more specifically, to the relative static and dynamic positioning of the body and its limbs. Ideally, in a body exhibiting good posture, the spine has no lateral curvature and the legs have little angulation in the knees and ankles. In addition, when viewed from the side, the spine forms a slight S-shape with the two curves of the S-shape being evenly disposed on opposite sides of an imaginary line extending downwardly from the head through the body's center. Such an alignment provides an even distribution of body weight over the spine and lower body joints resulting in a relatively uniform distribution of pressure on the intervertebral discs of the spine.

The effects of poor posture are well documented and include limited range of motion wherein muscles, such as the pectoral muscles in the chest, may be permanently shortened due to a hunched-over upper body position. Other effects of poor posture include discomfort in the form of headaches at the base of the skull and pain in the shoulders, arms, and hands. Additionally, poor posture may lead to pain in the jaw due to a forward-head position, as well as decreased lung capacity due to decreased volume of the chest cavity and lungs. One of the most common consequences of poor posture is the onset of lower back pain which may increase with advancing age. Finally, a hunched-over upper body position of poor posture can add years to one's appearance. Many attempts to improve posture involve the use of straps. For example, see U.S. Patent Application Publication No. 20050197607, published on Sep. 8, 2005, the entirety of which is incorporated by reference herein.

However, by assuming good posture, gravitational forces may be more evenly distributed through the bones, ligaments and muscles of the body. Maintaining good posture is equally important during passive (static) activities such as sitting and standing, as well as during dynamic activities such as walking, running, and lifting. Theoretically, the slight S-shape of the spine that is characteristic of good posture should preferably be maintained during both static and dynamic activities. Unfortunately, our increasingly sedentary lifestyle, wherein many hours are spent sitting in front of a computer, driving an automobile, or watching television, has an adverse effect on posture. Such static activities may result in forward protrusion of the head and neck, rounding of the thoracic and lumbar spine and stretching of the spinal ligaments. Such stretching gradually causes pain in the neck and upper back and results in fatiguing of the body's muscles and ligaments. Poor posture during dynamic activities such as running and lifting results in inefficient body movements with increased stress on muscles and ligaments.

Maintaining an awareness of proper posture during static and dynamic activities may sometimes prevent overstressing of muscles and ligaments. In addition, maintaining an awareness of proper posture may train certain muscles through muscle memory such that proper posture eventually becomes a habit. However, it is sometimes difficult to maintain an awareness of proper posture during mentally challenging activities such as working at a computer, or during physically challenging activities such as participating in aggressive sports. Physical therapists may utilize postural therapy to improve the posture of a patient. Such postural therapy may include techniques such as shoulder taping and breathing exercises. Conventional chiropractic techniques may utilize body manipulation and treatment to help keep the patient's spine in alignment. However, the patient must take the time and energy to visit the offices of a physical therapist or a chiropractor in order to receive the needed postural therapy and/or chiropractic manipulation. Moreover, alternative treatment, such as cutaneous nerve stimulation, is often overlooked as a method to improve the patient's posture.

In a preferred embodiment, the present invention is adapted to continuously train and develop certain body muscles and therefore optimal movement patterns, such that the user's static and dynamic posture may be improved. In addition, the present invention preferably allows for developing such muscle training during static activities such as standing and sitting. In addition, the present invention preferably discretely allows for developing such muscle training during dynamic activities such as walking, running and during other daily activities. Furthermore, the present invention preferably helps improve the user's posture and musculature such that it is progressively adjusted in accordance with changes or improvements in the user's posture or musculature over time. Finally, the present invention preferably helps improve and adjust the user's posture according to varying physiological parameters between users including differences in user's age, body size, muscular development and underlying pathophysiologic status.

SUMMARY OF THE PREFERRED EMBODIMENTS

The invention is a posture improvement or sensory motor stimulation device that is adapted to provide neuromuscular stimulation or proprioceptive therapy using a combination of gripping of the skin, pressure, torque and angle simultaneously applied to the user in order to train body muscles for proper posture through muscle memory. The device comprises a garment designed to be worn by a user and which is adapted to envelop at least a portion of the user's torso and, in at least one embodiment, at least a portion of the user's upper arms. This garment is preferably configured like a short-sleeved undershirt or T-shirt. However, it can also be configured like a tank top, long sleeve shirt, sleeveless shirt, etc. The garment is often referred to herein generically as a shirt. It will be understood that this covers all embodiments of the garment that are worn on the user's torso.

Pressure is applied to the user's skin in order to apply specific pressure to the skin to stimulate the cutaneous nerve receptors, thereby resulting in enhanced proprioception and enabling the wearer to self correct body alignment and posture. Mechanoreceptors are sensitive to pressure, stretch, torque on muscles, tendons, joint lining, etc. These are the receptors that help the wearer to adjust and adapt. The nociceptor is also stimulated by the design of the garment and reacts by decreasing neurotransmitter frequency and causes an instant decrease in pain. This is done preferably by configuring the garment as a relatively tight, form-fitting shirt. The garment is adapted to envelop at least a portion of the user's torso and at least a portion of the user's upper arms. The garment has an inner and an outer surface, a front side, a back side, opposing lateral sides, and a pair of partial sleeves. The front side includes a chest portion and a stomach portion, while the back side includes a back portion. The garment also defines opposing shoulder portions and a waist portion extending about a lower end of the garment. A short-sleeved version of the garment allows for effective training of the user's pectoralis major muscles located in the user's chest. In addition, the short-sleeved configuration of the garment enhances the user's range of motion, particularly at the shoulder joints, in addition to providing conditioning of the user's rotator cuffs. This short sleeved version allows for effective retraining of the overused and understretched pectoralis minor and major, serratus, subscapularis muscles. It three dimensionally balances muscles of the chest, neck, under arms, upper back and inter scapula. It also simultaneously aligns the spine and joints of the upper extremities allowing for improved range of motion, optimized biomechanics and improves overall function and recovery.

The garment may be fabricated of a stretchable, yet taut material in order to provide the desirable form-fitting feature such that specific pressure may be readily applied to the surface of the skin over specific anatomical landmarks for neuromuscular stimulation. In this regard, the garment is preferably fabricated of elastomeric material that is also preferably breathable and/or which has moisture wicking capabilities such as may be provided by a material comprised of a combination of LYCRA® and spandex, FABRIFOAM®, nylon or the like.

More particularly, there is provided a garment for sensory motor stimulation/retraining of the wearer, which comprises an anterior portion and a posterior portion joined to the anterior portion. Each of the anterior portion and the posterior portion are fabricated of a thin, elastomeric material which is form-fitting, in order to apply pressure to the surface of the wearer's skin to enhance neuromuscular stimulation thereto. A proprioceptive panel is integrated with the posterior garment portion and positioned to extend over the upper back or inter scapular region of the wearer. The proprioceptive panel is fabricated of an elastomeric material and having characteristics which cause the garment to stimulate optimal scapular position. In one embodiment, the proprioceptive panel is comprised of the same elastomeric material as the posterior portion. In an alternative embodiment, the proprioceptive panel is comprised of a heavier, more dense elastomeric material than that comprising a remainder of the posterior portion.

In some embodiments of the present invention, the inventive garment further comprises an elastic band disposed on the proprioceptive panel. This elastic band is fabricated of a stronger elastomeric material than that comprising the proprioceptive panel, and is positioned to substantially coincide with the inferior medial border of the wearer's scapula.

In a presently preferred embodiment of the present invention, the proprioceptive panel is positioned to extend along substantially an entire length of the spine of the wearer.

The inventive garment preferably further comprises at least one and preferably a plurality of shoulder strap portions positioned to extend from the proprioceptive panel upwardly and over the wearer's shoulder toward the garment anterior portion. The shoulder strap portion is integrated with the garment posterior portion and is comprised of elastomeric material.

In one embodiment, the proprioceptive panel is generally triangular in shape, positioned to extend downwardly from the shoulders of the wearer toward an apex positioned to be disposed at approximately the small of the wearer's back.

Preferred embodiments of the invention further comprise at least one and preferably a plurality of arm strap portions extending from the proprioceptive panel and positioned to proceed about an arm of the wearer toward the anterior portion of the garment. The arm strap portions are integrated with the garment posterior portion and are comprised of elastomeric material. Nerve receptor stimulators are preferably disposed on an inner surface of the garment, for contacting the wearer's skin and creating additional proprioceptive stimulation when the garment is worn. These nerve receptor stimulators preferably comprise a plurality of strategically placed neuro nubs, comprising soft, tacky bumps and extending inwardly from the inner surface of the garment. Alternatively, the nerve receptor stimulators may comprise proprioceptive viscoelastic pads.

In preferred embodiments, the material comprising each of the anterior and posterior portions also comprises a moisture wicking material. The proprioceptive panel is stitched to the posterior portion, though it may also be joined by alternative methods as well. One possibility is to integrate the panel into the posterior portion of the garment by blending it into the base material forming the posterior portion, using advanced production techniques, forming a single, seamless, composite layer.

In another aspect of the invention, there is disclosed a method of making a garment for proprioceptively treating a wearer. This method comprises a step of joining a posterior portion to an anterior portion of the garment together, wherein each of the posterior portion and the anterior portion are comprised of a thin, elastomeric material, so that the joined posterior and anterior portions form a garment resembling a shirt. The method further comprises a step of joining a proprioceptive panel, comprised of an elastomeric material, to the posterior portion, in a location wherein when the garment is worn by a user, the proprioceptive panel is disposed over at least a portion of the user's spine and inter scapular region. These steps may be performed in interchangeably, as they are not sequence dependent. In one presently preferred embodiment, the joining steps are performed by stitching the posterior portion and the anterior portion together, and stitching the proprioceptive panel to the posterior portion. In some embodiments, the proprioceptive panel comprises a second layer of material over the base material forming the posterior portion. In other embodiments, the proprioceptive panel is integrated with the posterior portion in such a manner that only a single layer of material results.

The shirt creates a sensation/cue on the skin through the design that specifically bends, compresses and directs the nerve receptors in the skin (peripheral nervous system 20-80 nerve endings/square inch on skin, in muscles, tendons, joint lining, etc.) to be pulled in such a way and in such a specific direction that tells the brain to instantly relax and lengthen specific, over used, under stretched muscles while the brain simultaneously commands the opposite (front to back and/or side to side), weak, under toned, under supportive muscles to contract, tone and support the wearer's core and torso. This natural reflexive response is known as reciprocal inhibition and this naturally balancing muscle stimulation system retrains the wearer's muscles every time the garment is put on to create a wearable, therapeutic short/pant that decreases muscle and joint pain, improves recovery from training, travel and injury and improves aberrant biomechanics that create muscle imbalances that are the major cause of most musculoskeletal injuries today. In a preferred embodiment, the desired cues and responses are provided by straps or bands that twist the wearer's body, tissues or muscles in a spiral manner. Spirals and spiral physiology are naturally occurring within the human body and nature as a whole and can all be related through the Fibonacci numbers or Fibonacci structure. The Fibonacci numbers are nature's numbering system. They appear everywhere in nature, from the leaf arrangement in plants, to the pattern of the florets of a flower, the bracts of a pinecone, or the scales of a pineapple. The Fibonacci numbers are therefore applicable to the growth of every living thing, including a single cell, a grain of wheat, a hive of bees, and even humans.

The Fibonacci sequence is 1, 1, 2, 3, 5, 8, 13, 21, 34, 55, and so on. It begins with the number 1, and each new term from there is the sum of the previous two. The limit ratio between the terms is 0.618034 . . . , an irrational number variously called the "Golden Ratio" and/or the "divine proportion," but in this century more succinctly "PHI" (f) after the architect Phidias, who designed the Parthenon. In other words, any two adjoining numbers equal the next higher number. For example, 5+8=13. Any number divided by the next higher number gives a ratio of 0.618. For example, 8/13=0.618. Any number divided by the next lower number gives a reciprocal of 1.618.

In the lower numbers the ratios are not exact, but close enough for practical purposes. Both the Fibonacci sequence and the Golden Ratio appear in natural forms ranging from the geometry of the DNA molecule (and the human body) to the physiology of plants and animals. In recent years, science has taken a quantum leap in knowledge concerning the universal appearance and fundamental importance of Fibonacci mathematics. Some of history's greatest minds, from Pythagoras to Isaac Newton, have held phi (f) and the Fibonacci sequence in the highest esteem and reverence.

All human senses, including hearing, touch, taste, vision and pain receptors, have not only spiral physiology, but also response curves that are logarithmic (having a fibonacci structure). Cellular action membrane potentials, which are important for muscles and the nervous system, have a voltage equal to the log of the ratio of the ion concentration outside the cell to that of inside the cell. The brain and nervous systems are made from the same type of cellular building units and look similar microscopically, so the response curve of the central nervous system is probably also logarithmic. This spiral/helical physiology is utilized by the design of the garment of the present invention. The straps extend about the axis of the wearer's torso.

The design stimulates the sensory motor system (sensori includes the nervous system combined with the (motor) musculoskeletal system), instantly cueing a wearer's upper body into muscular balance and ideal anatomical alignment. This stimulates the user's anatomy on both a conscious and subconscious level. This instantly allows the wearer to move with more biomechanical efficiency which means using less energy while enhancing and optimizing body mechanics. This has an effect that decreases normal wear and tear on joints and enhances healthy circulation and recovery from training, travel, and injury.

It will be appreciated that virtually every time a user puts the garment on, he/she is training. The garment makes weak muscles work. When a weak muscle works it helps to balance the muscles so the body is using all sides to work with rhythm and synchrony making the body move with more efficiency, greater fluidity and less effort. The garment supports and protects the joint structures by enhancing the body's dynamic restraint system.

Another embodiment of the invention, where the sensory motor system stimulation features are positioned on the inside of the garment. This embodiment is preferably a fusion of the latest technical fabrics and space age materials combined with the most recent scientific research in functional human physiology, fitness and performance, anatomy and the sensory motor system. The garment or shirt preferably increases sensory motor stimulation to muscles that are commonly found to be imbalanced and dysfunctional and interfaces with the human sensory motor system. In use, the shirt enhances the constant feed forward, feed back system so the wearer's body can more effectively both consciously and subconsciously, adapt to the proprioceptive information provided to the sensory motor system when the shirt is worn. The inside of the shirt is lined with special thermo elastic plastic or rubber bands or straps that contact the cutaneous nerve receptors in the skin with specifically designed angles, lengths and densities that apply different pressures and directional pull. This embodiment also helps decrease shirt migration that occurs with wearers who are very active in the shirts.

In a preferred embodiment, bands or straps can be placed in the following areas of the shirt: 1. Transverse abdominus stimulation and support, which is crucial for full function core strength. 2. Internal abdominal oblique stimulation and support, which is important for core stability and function. 3. Thoracic extension stimulation and support, which begins at the first thoracic vertebra and interlocks each vertebral segment down to T12 and preferably provides a spring back effect because the spinal erector muscles are cued/stimulated to contract when the wearer lets his/her head and spine slump forward. In other words, the rubber in the garment that is positioned over the thoracic spine prevents the normal stretch of the skin when the head drops forward. This is what stimulates the cutaneous nerve receptors to cause the muscles to respond appropriately. 4. Lower rectus abdominus stimulation and support. The bands that compress and stimulate lower abdominal tone and support the lumbosacral spine and core, adding tone to the lower abs while simultaneously decreasing hip flexor tone (dominance) and hyper lordosis (pot belly and butt out) that are common in society today. 5. Flexible lumbar mobility support, which provides compression and proprioceptive stimulation to enhance natural support and mobility of the lumbosacral spine. 6. Interscapular area of shirt uses horizontal bars (may be slightly angled to fit natural anatomy) that can be increased or decreased in size, elasticity and density (depending on the wearer or desired effects) to provide the most desirable level of interscapular support depending on posture fitness, injury, health objectives, etc. 7. Also lining the inside of the shirt in a preferred embodiment, are neuro nub sensors or neuro nubs that are placed in specific and very richly innervated acupuncture meridian points. The neuro nubs bend and massage these points every time the wearer moves a muscle (adjacent to the nubs). This increases circulation and what Chinese medicine refers to as CHI or life energy directly to these areas that are commonly found to be out of balance and have restricted or congested chi.

This embodiment of the shirt is designed to stretch where the muscles most commonly are tight and over used while simultaneously sending cues to under used, under toned muscles to tone muscles to contract, tone and add support. The shirt is preferably manufactured in a seamless style that better conforms to the intimate curves and shapes of the body making the shirt comfortable whether the wearer is training, competing or recovering in it. Over time, just as the body adapts to negative information (like sitting at a computer and slumping), it will adapt and remodel to new, "positive" information.

In accordance with one preferred embodiment of the present invention, there is provided a garment adapted to be worn by a wearer that includes an outer layer configured to be worn over at least a portion of the wearer's torso. The outer layer has an anterior portion, a posterior portion, an inner surface and an outer surface. The garment also includes at least one sensory motor stimulation member affixed to the inside surface of the outer layer. When the garment is worn by a wearer the at least one sensory motor stimulation member contacts a portion of the wearer's skin and when the wearer moves the at least one sensory motor stimulation member alters the normal stretch of the portion of the skin contacted by the at least one sensory motor stimulation member, thereby stimulating the wearer's cutaneous nerve receptors to cause the wearer's muscles to respond appropriately.

In accordance with another preferred embodiment of the present invention, there is provided a garment for stimulation of a wearer's sensory motor system. The garment includes a main body portion that includes an anterior portion and a posterior portion and at least one sensory motor stimulation member associated with the main body portion. The garment is configured to be worn over at least a portion of the wearer's torso and is form-fitting when worn by the wearer. The at least one sensory motor stimulation member contacts a portion of the wearer's skin when the garment is worn and is fabricated of an elastomeric material that causes the garment to stimulate the cutaneous nerve receptors in the portion of the wearer's skin contacted by the at least one sensory motor stimulation member. In a preferred embodiment, the at least one sensory motor stimulation member includes at least one of a shoulder strap, upper arm strap, serratus strap, diamond shaped plate, lower ab band, thoracic vertebra patch, scapular band and lumbar spine band. In another preferred embodiment, the main body portion defines a generally vertically extending axis and the at least one sensory motor stimulation member is positioned such that it extends in a spiral about the axis of the main body portion In accordance with another preferred embodiment of the present invention, there is provided a method that includes donning a garment that covers at least a portion of the wearer's torso and moving while wearing the garment. The garment includes a main body portion, at least one sensory motor stimulation member associated with the main body portion and is form-fitting. The at least one sensory motor stimulation member contacts a portion of the wearer's skin. The method also includes stimulating the cutaneous nerve receptors in the portion of the wearer's skin contacted by the at least one sensory motor stimulation member. In a preferred embodiment, the method also includes the step of removing and donning the garment a plurality of times over a period of time. At the end of the period of time the muscles positioned under the at least one sensory motor stimulation member are in a more optimal position than at the beginning of the period of time. Optimal means that there is a balance between agonist and antagonist muscles as they support human structure versus the common effects of gravity. In other words, what a person of ordinary skill in the art would consider perfect posture.

In accordance with yet another preferred embodiment of the present invention, there is provided a device adapted to be worn by a wearer. The device includes a main body portion configured to be worn over at least a portion of the wearer's torso and means, associated with the main body portion, for stimulating a plurality of the wearer's cutaneous nerve receptors when the wearer moves its torso when wearing the device. The main body portion includes an anterior portion, a posterior portion, an inner surface and an outer surface. In a preferred embodiment, when the device is worn by the wearer and the wearer moves, the means for stimulating a plurality of the wearer's cutaneous nerve receptors alters the normal stretch of the portion of the skin contacted by the means for stimulating a plurality of the wearer's cutaneous nerve receptors.

The invention, together with additional features and advantages thereof, may be best understood by reference to the following description taken in conjunction with the accompanying illustrative drawings. In these accompanying drawings, like reference numerals designate like parts throughout the figures.

BRIEF DESCRIPTION OF THE DRAWINGS

Like numerals refer to like structures or features throughout the several views of the drawings.

DETAILED DESCRIPTION OF THE PREFERRED EMBODIMENTS

Figure 1:
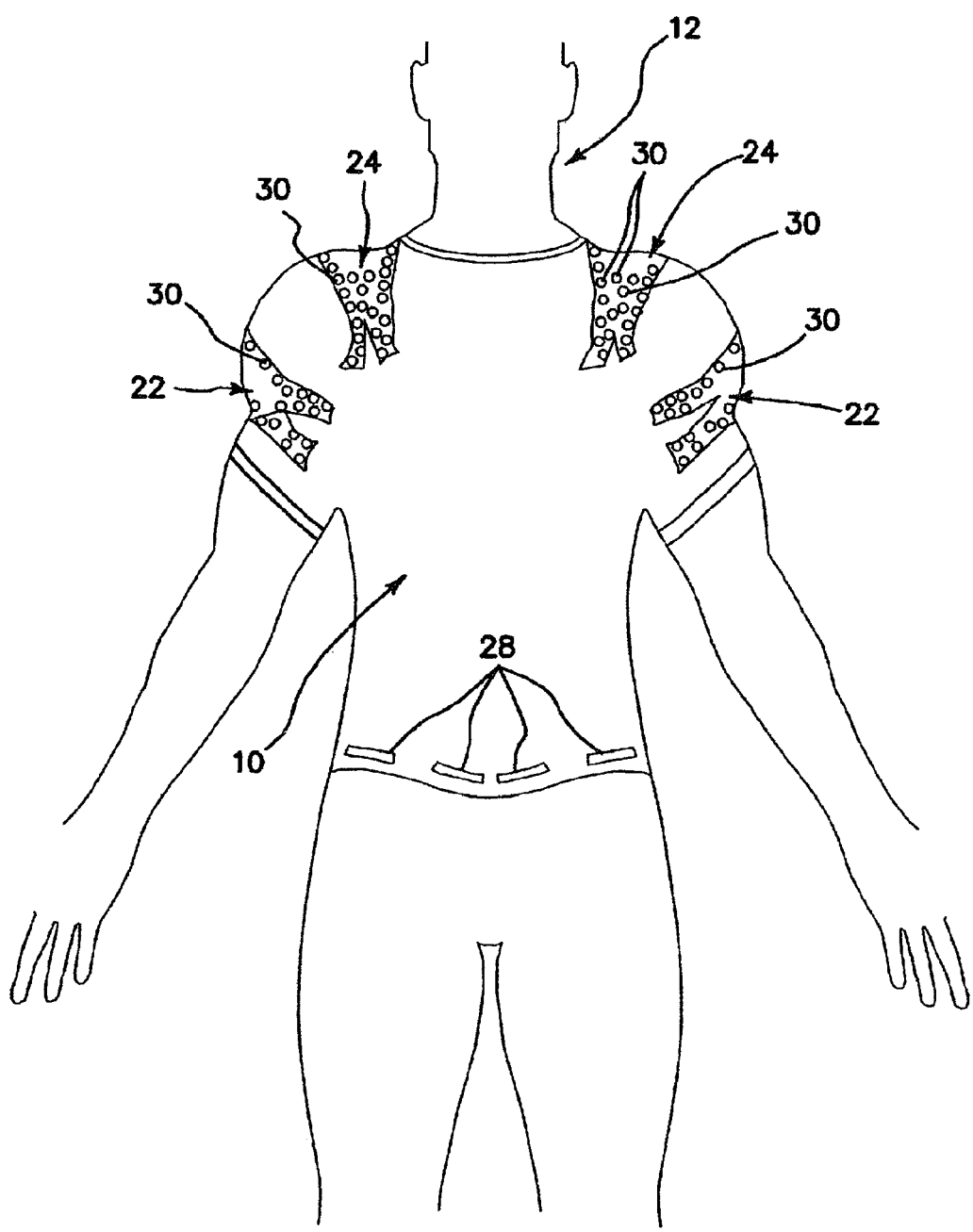
FIG. 1 is an anterior view of an embodiment of the garment of the present invention, being worn by a user.

As shown in the drawings, for purposes of illustration, preferred embodiments of posture improvement garments are shown and described. It will be appreciated that terms such as "front," "back," "top," "bottom," "side," "short," "long," "up," "down," and "below" used herein are merely for ease of description and refer to the orientation of the components as shown in the figures. It should be understood that any orientation of the garments and the components thereof described herein is within the scope of the present invention.

Figures 2, 2A:
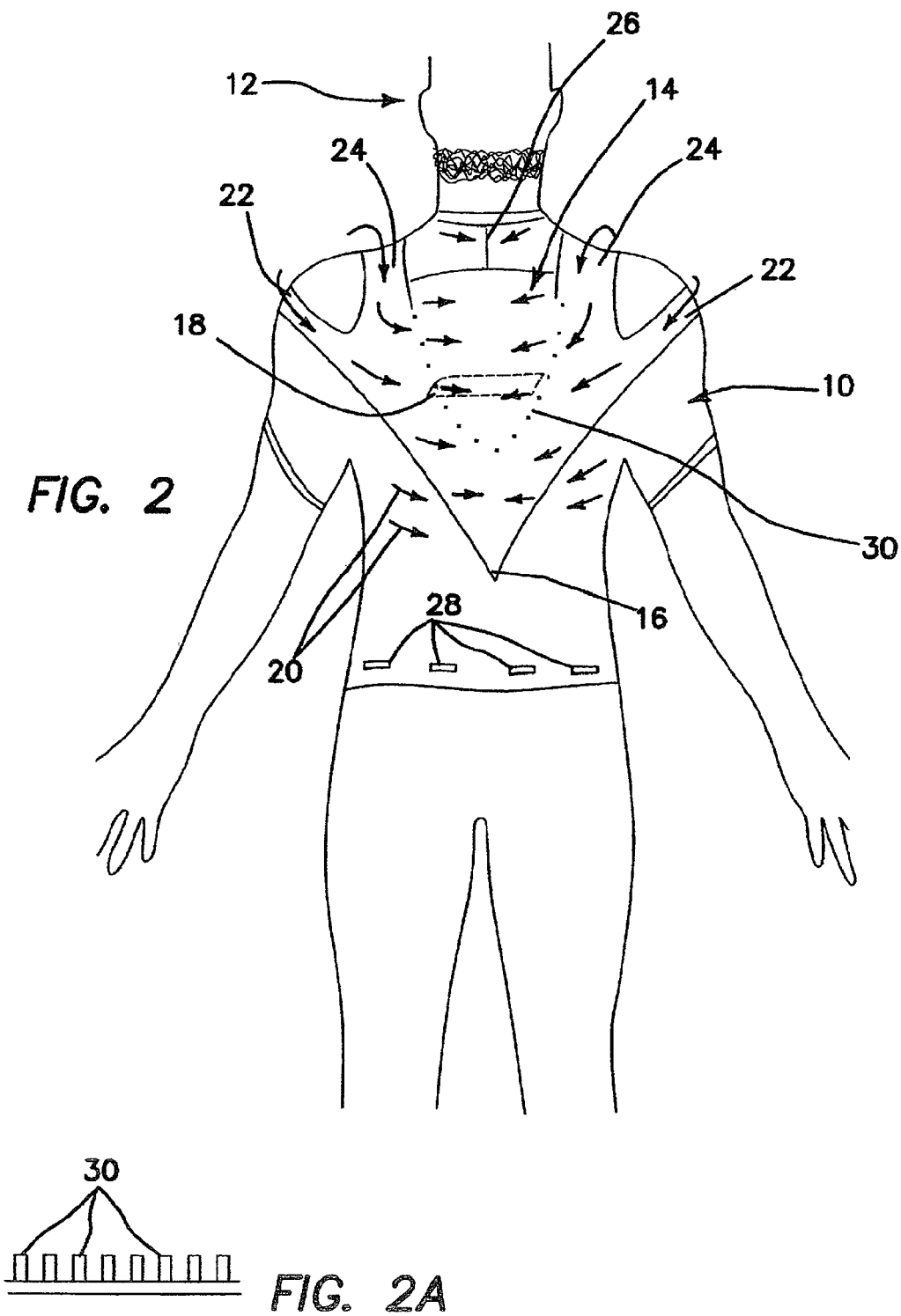
FIG. 2 is a posterior view of the garment of FIG. 1.
FIG. 2A is a side view of a section of neuro nubs for use with the garments of the invention.

Referring now to the drawings, wherein the showings are for purposes of illustrating the present invention and not for purposes of limiting the same, FIGS. 1 and 2 are views of a first embodiment of a posture improvement garment 10, which is configured to be worn by a user 12 and which is configured to envelop at least a portion of the user's torso and at least a portion of the user's upper arms. In this regard, the garment 10 is generally configured to be similar to one of a short-sleeved undershirt, T-shirt, or polo shirt. While the illustrated garment 10 is designed as a "pull-over" style, the garment may also be provided with an open or partially open front or back portion, which is selectively closeable by means of known garment closure systems, such as a zipper, buttons, snaps, and the like. Such a style eases the wearability of the garment because it can be put on or removed without pulling the garment over one's head.

The embodiments illustrated in the aforementioned '656 application have been shown to have a remarkable proprioceptive therapeutic effect on the wearer, substantially improving his/her posture and relieving pain related to poor posture and related muscle strain. However, the illustrated embodiments in that application are not particularly adapted for use in casual recreational and social settings, or for routine retail sale to consumers. Because of the external strapping, if they are to be worn in such settings, aesthetics dictate that they be worn under external garments, which must be relatively bulky and heavy to adequately cover the therapeutic garment. Accordingly, the present invention performs many of the same functions as the prior embodiments disclosed in the '656 application without the use of external strapping. Similar proprioceptive effects are achieved by the use of strategically placed stretch panels and proprioceptive pads, integrated directly into the material used to fabricate the garment. As a result, the garments of the present invention are particularly suited for the consumer market, as they are attractive and comfortable.

Regarding material from which the garment 10 may be fabricated, it is preferred that the material be thin, and have an elastic quality that stretches or moves with the user's body, in order to provide a desirable form-fitting feature such that pressure may be readily applied to the surface of the user's skin in order to enhance neuromuscular stimulation thereto. The material may contain, but not be limited to, polyester, spandex, elastic, nylon, and the like. It may have metal ions woven into it, or other mechanical sweat wicking, temperature regulating materials which are known in the art and function in an equivalent way to regulate temperature and wick moisture. Its breathability and/or moisture wicking capabilities function to improve the user's comfort level during periodic wearing of the device 10.

Referring particularly to FIG. 2, there is shown a elastic stretch panel or proprioceptive posture patch 14. As shown, the patch 14 is generally triangular in shape (its border is represented by the dotted outline in the drawing), and is welded or sewn into the upper back, or inter scapular region, extending downwardly from both shoulders of the user 12 to a point 16 disposed at the small of the user's back. The proprioceptive posture patch 14 is fabricated of an elastic material, which may be the same as that from which the garment 10 is fabricated, or it may alternatively be a heavier, more dense elastic material to assist in support of relatively weak middle or lower trapezious, rhomboids major and minor, and serratus musculature respectively. The purpose of the patch 14 is to stimulate optimal scapular position and spinal alignment. This is the functional base for optimal posture and scapular kinematics. The patch may be disposed as a second layer atop the base layer of the garment, or may alternatively be blended (integrated) into the garment material, using suitable production techniques, to form a single composite layer.

In a preferred embodiment, an elastic band 18 is employed in about the midpoint of the patch 14, which is fabricated of stronger elastic than that used for the patch 14. The band 18 is positioned to substantially coincide with the inferior medial border of the scapula.

As demonstrated by the arrows 20, the base layer of the garment 10 has a posterior (retracting) directional influence on the body of the user 12.

Referring now to FIG. 1, as well as FIG. 2, two upper arm straps 22 and two shoulder straps 24 begin on the anterior side of the garment 10 (FIG. 1) and continue around to the posterior side, as shown (FIG. 2). These straps 22, 24 are built into the garment 10, in much the same way as the patch 14. The arm straps 22 are designed to provide a specific directional pull on the infraspinatus and teres minor muscles. The shoulder straps 24 are designed to influence problems relating to posterior scapular tilt, in part by influencing the pectoralis minor muscle adjacent to the coracoid process.

Darts 26 (FIG. 2) may be used to enhance posterior pull/cue to help the scapula to attain an optimal position.

As can be seen in each of FIGS. 1 and 2, viscoelastic tape 28 may be disposed about the hem of the garment 10, for the purpose of preventing migration of the garment. Alternative means providing a tacky surface for contacting the user's skin may instead be used.

It should be noted that the specific angles of arrows shown in FIG. 2 may indicate coupled motion influence upon the axis of the scapula, caused by the various elastomeric elements of the garment 10.

The various dots 30 shown in FIGS. 1 and 2 are neuro nubs. These neuro nubs are more particularly shown in FIG. 2A. These neuro nubs 30 preferably comprise soft, tacky bumps, or cutaneous nerve receptor stimulators, which are designed to provide a massaging, stimulating effect when the user moves. As shown, these nubs 30 are disposed on each of the straps 22 and 24, where they stimulate portions of the body adjacent to rotator cuff muscle attachment points on the humerus, as well as pectoralis minor muscles in the vicinity of the coracoid process. In general, the inventor has found that patterns of such neuro nubs 30 are helpful in creating proprioceptive stimulation, and also function to provide decreased migration of the garment 10 as the body moves throughout its full range of motion. They are disposed at specific areas on the inside surface of the garment, to stimulate cutaneous nerve receptors in the skin and soft tissue structures to enhance "noise" that creates cues to the brain, enhancing muscle balance, body position awareness, posture, function, and performance.

Desired locations of the neuro nubs 30 are at known acupuncture sites, as stimulation of these specific energy meridians enhances blood flow and stimulates normal physiology to organs and soft tissues that supply movement, support, and information crucial to those seeking optimal health and function.

Although one elastic panel 18 and four elastic straps 22, 24 are shown in the embodiment of FIGS. 1 and 2, a plurality of such panels 18 and/or straps 22, 24, of various shapes and sizes, may be employed if desired. As noted, the stretch panels 18 and straps 22, 24 may be constructed of the same or similar materials as the garment 10 or patch 14. The panels 18 and straps 22, 24 function to stimulate muscles that are too tight (the panels/straps will stretch these muscles), or too loose and undertoned (the panels/straps will add tone to these muscles and encourage/stimulate them to work). Conventional approaches to date have focused on mechanical support systems that have been shown to create atrophy and a reliance on a brace, which in the long term can create a system of dependence that the inventor believes is detrimental to optimal health and efficient recovery and performance. The elastic or stretch panels/straps as well as the patch(es) 14, on the other hand, create specific traction and tactile stimulation of cutaneous nerves in the skin. There are a minimum of 20,000 of such nerves per square inch of skin that will transfer specific information to the receptors (mechanoreceptors/nociceptors) that exist by the thousands/millions in the muscle, tendon, ligament, and joint surfaces, causing a predictable unloading of specific, predictable and common muscle imbalances that create and perpetuate joint stress and injury throughout the body.

Figure 3:
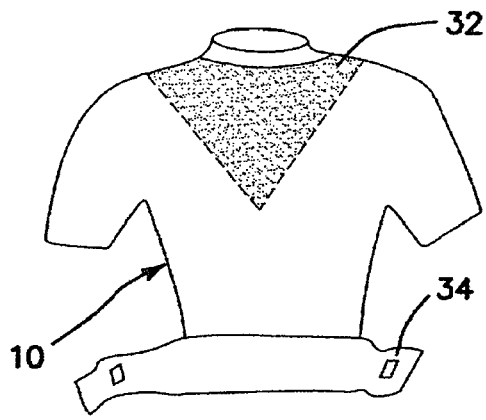
FIGS. 3-5 are sequential views of another embodiment of a garment of the present invention, illustrating a sequence of fabrication of the garment to include the advantageous posture-improving features of the invention.
Figure 4:
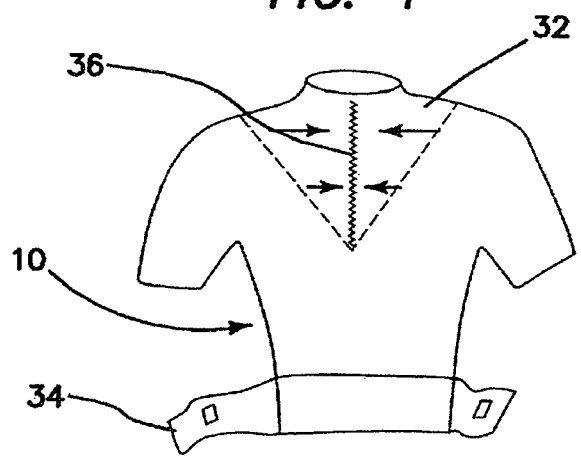
Figure 5:
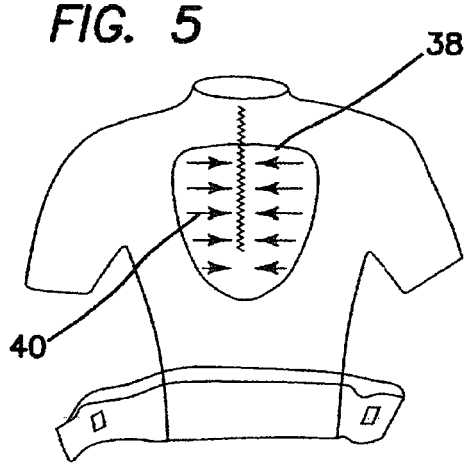
Figure 6:
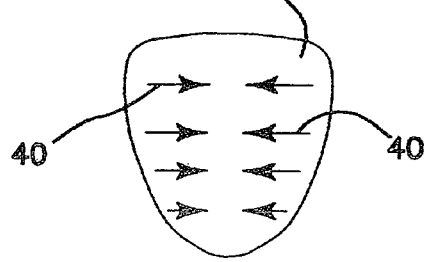
FIG. 6 is a view, in isolation, of a specific tension elastic posture patch for use in fabricating the garment of FIGS. 3-5.

Now referring to FIGS. 3-6, there is shown a somewhat modified embodiment of the garment 10 of the invention. The posterior side of the garment is shown. The views in FIGS. 3-5 are sequential, wherein, as shown in FIG. 3, a V 32 has been cut out of the shirt. In this embodiment of the invention, an optional belt or strap 34 is provided at the base of the garment 10. As shown in FIG. 4, the edges of the V 32 have been sewn together along seam 36. Then for additional support, an elastic posture patch 38 is applied over the seam 36 as shown. The elastic patch 38 is adapted to apply specific tension along arrows 40 to assist the user's posture, as discussed above.

Figure 7:
FIG. 7 is an anterior view of still another embodiment of a garment of the present invention.
Figure 8:
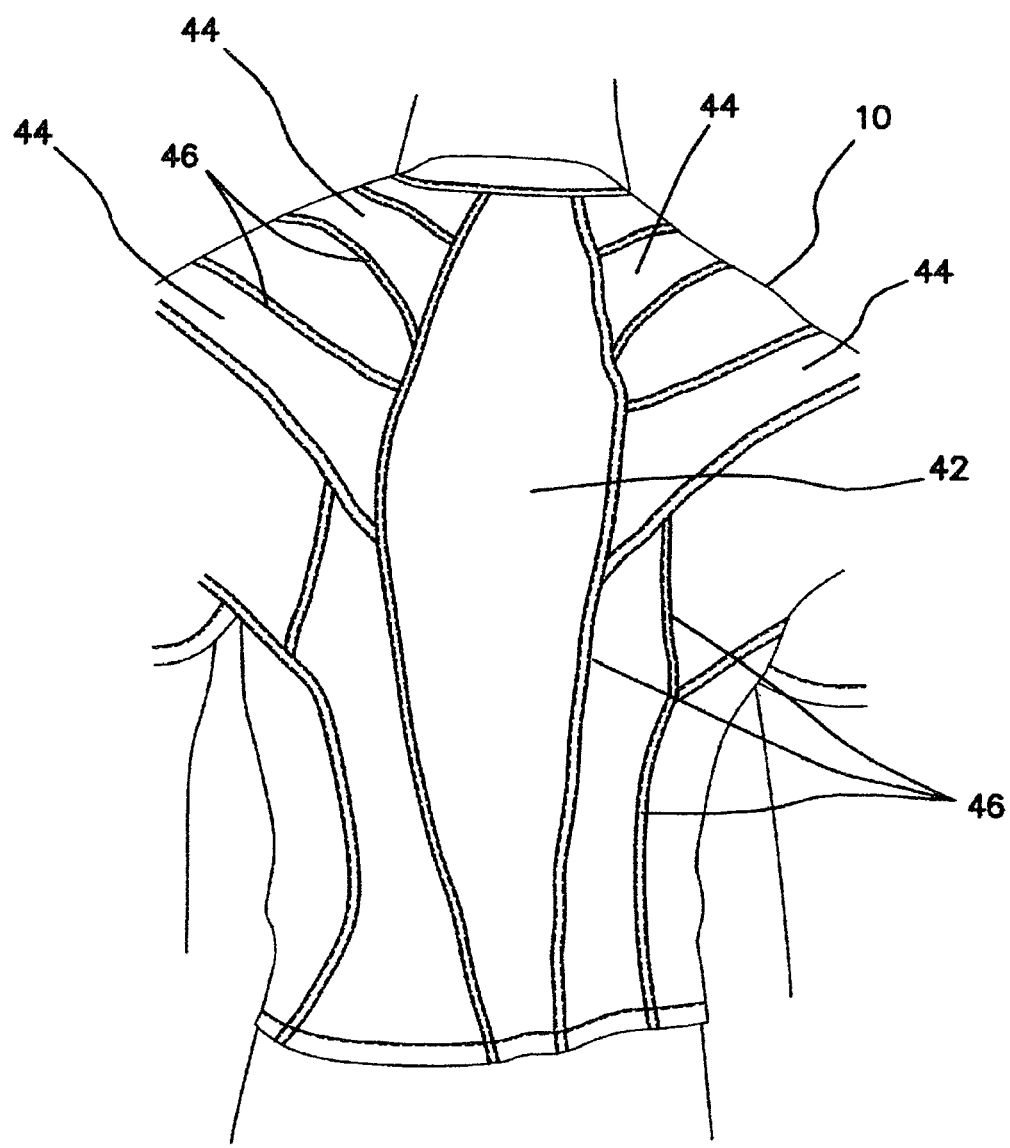
FIG. 8 is a posterior view of the embodiment of FIG. 7.

Still another, presently preferred, embodiment of the garment 10 of the invention is illustrated in FIGS. 7 and 8. This embodiment is similar in many respects to the prior embodiments, but employs an elastic or stretch band or panel 42 which extends along substantially the entire length of the spine of the wearer, as shown in FIG. 8. Straps 44 are also provided, which extend, as shown, from the patch 42 up and over each shoulder of the user. The straps 44 preferably extend over the shoulder and onto the anterior side of the garment, as shown in FIG. 7. The panels 42, 44 are integrated into the remainder of the garment 10 by stitching 46. This configuration has been found to substantially increase and enhance the cues which proprioceptively stimulate the user's brain and body to a corrected posture.

Significantly, in all of the illustrated embodiments, the posterior panel of the shirt is smaller than the anterior panel (which are sewn together), preferably by about two inches. This increases the retractive pull of the shirt, and thus the compression applied to the user's skin.

Proprioceptive viscoelastic pads may optionally be employed in each of the illustrated embodiments, on the inside surface thereof, either permanently or releasably mounted thereto, for contacting the user's skin at strategic locations in order to increase the proprioceptive effect of the garment. These pads, preferably made of silicone, have a skin-contacting surface which is grooved or otherwise modified to improve tactile response, using an acupuncture-type approach. The pressure generated by the garment 10 creates an acupressure effect. In one embodiment, two of these pads may be deployed on the chest region of the user, while two others are deployed on the scapula border, but, of course, the strategic locations and numbers of pads may be varied in accordance with specific therapeutic objectives.

To summarize, the present invention uniquely functions, due to its proprioceptive approach, to address the following conditions:
  a) upper trapezium pain,
  b) rotator cuff weakness, by optimizing scapular position to improve the rotator cuff muscle,
  c) mid-thoracic pain, by decreasing tension in the periscapular muscles,
  d) scapular dyskinesis,
  e) biceps tendinitis,
  f) thoracic outlet syndrome,
  g) impingement syndrome, and
  h) glenohumeral instability.

Figure 9:
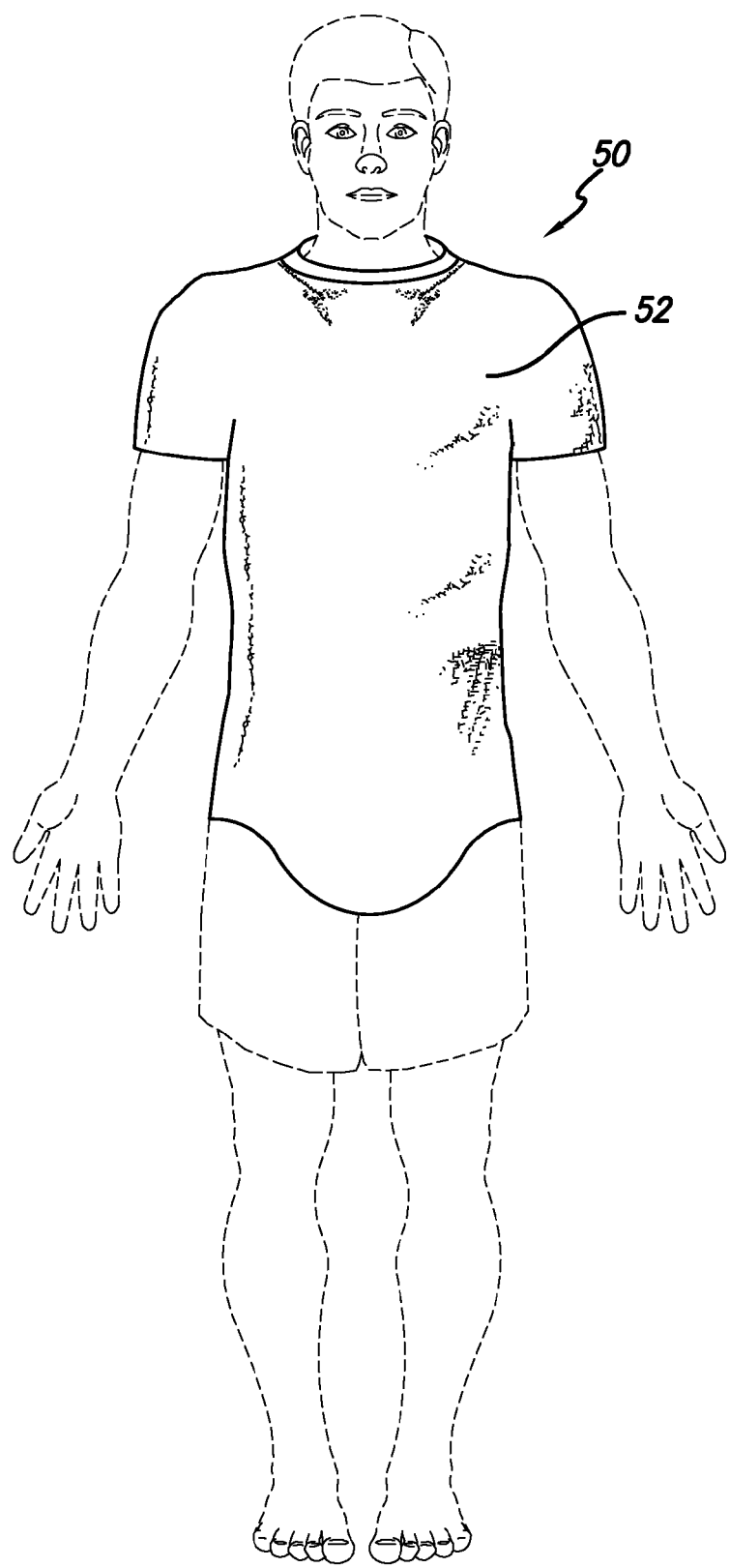
FIG. 9 is a front elevational view of a garment in accordance with another embodiment of the present invention.
Figure 10:
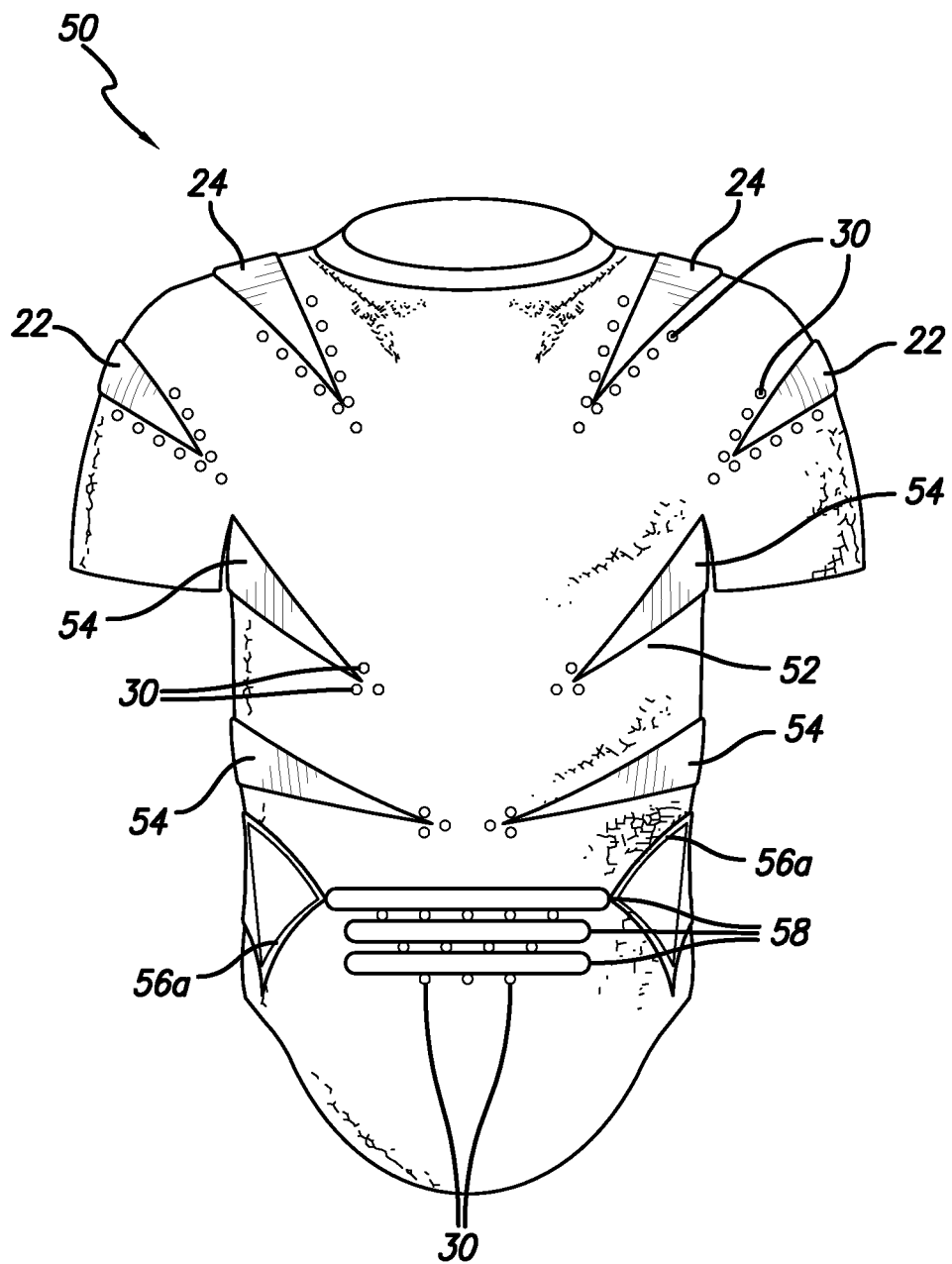
FIG. 10 is a front elevational view of the garment of FIG. 9 shown inside out to show the features on the inside of the garment.
Figure 11:
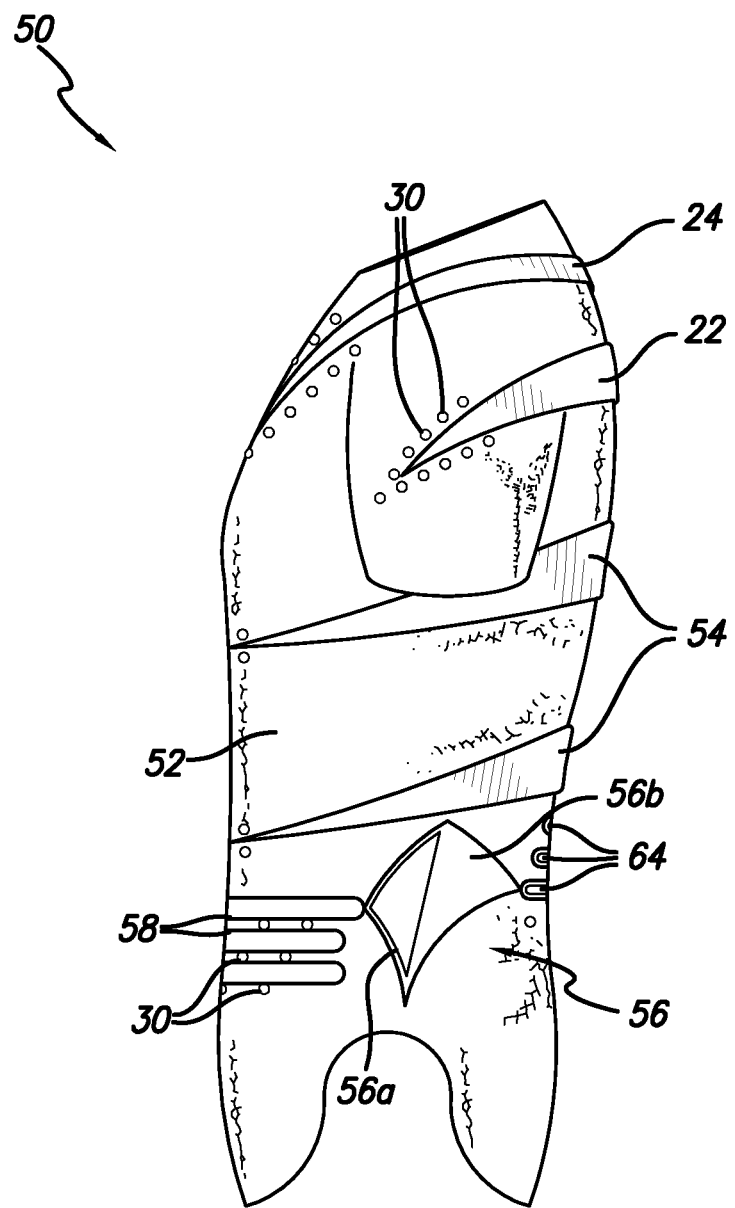
FIG. 11 is a left side elevational view of the garment of FIG. 9 shown inside out to show the features on the inside of the garment.
Figure 12:
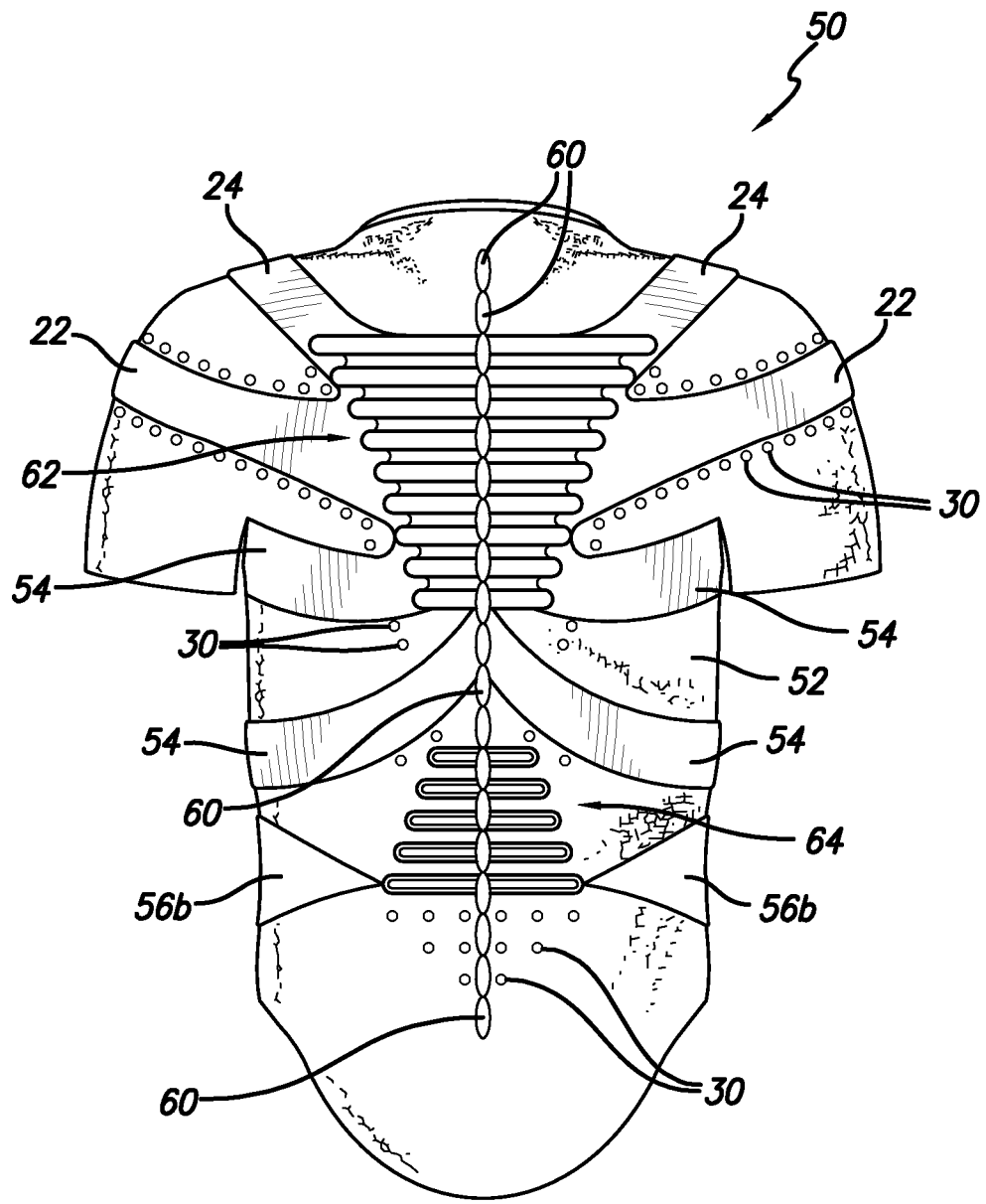
FIG. 12 is a rear elevational view of the garment of FIG. 9 shown inside out to show the features on the inside of the garment.

FIGS. 9-14 show another embodiment of a posture correcting or sensory motor system stimulating garment or shirt 50. As shown in FIG. 9, in a preferred embodiment, the garment 50 looks like a normal shirt from the outside, but includes features for stimulating the sensory motor system on the inside, as shown in FIGS. 10-12. However, this is not a limitation on the present invention. In a preferred embodiment, the main body portion, base portion or outer layer 52 of the garment 50 is formed as a shirt and is fabricated from a material such as polypropylene, LYCRA®, spandex, nylon or the like. Any material that allows the garment 50 to be form fitting is within the scope of the present invention. And, as described below, the proprioceptive or sensory motor stimulating features are affixed to the inside surface of the main body portion 52. In a preferred embodiment all of the proprioceptive or sensory motor stimulating members (including, but not limited to straps 22, 24 and 54, bands 18, 42, 58, 62 and 64, patches 14, 38 and 60, plates 56, neuro nubs 30, darts 26, viscoelastic tape 28—sometimes referred to collectively herein as "sensory motor stimulation members") are comprised of a material that alters and controls the amount of stretch in the base fabric (comprising the main body portion 52) of the garment 50 and prevents the normal stretch of the skin (in contact with a sensory motor stimulation member) when the wearer moves, thereby stimulating the wearer's cutaneous nerve receptors to cause the wearer's muscles to respond appropriately. For example, any elastomeric material, a thermo-elastic plastic, rubber or a material such as FABRIFOAM® can be used. The normal stretch of the skin is the amount of movement the skin makes when a person without a garment on moves. In another embodiment of the present invention, the shirt can comprise an entire layer of the sensory motor stimulating material (grip material) as the outside layer and a plurality of "non-grip patches" on the inside thereof. This is essentially the opposite of the embodiment described herein. The "non-grip" portions are the portions of the garment where no sensory motor stimulation is desired.

Figure 13:
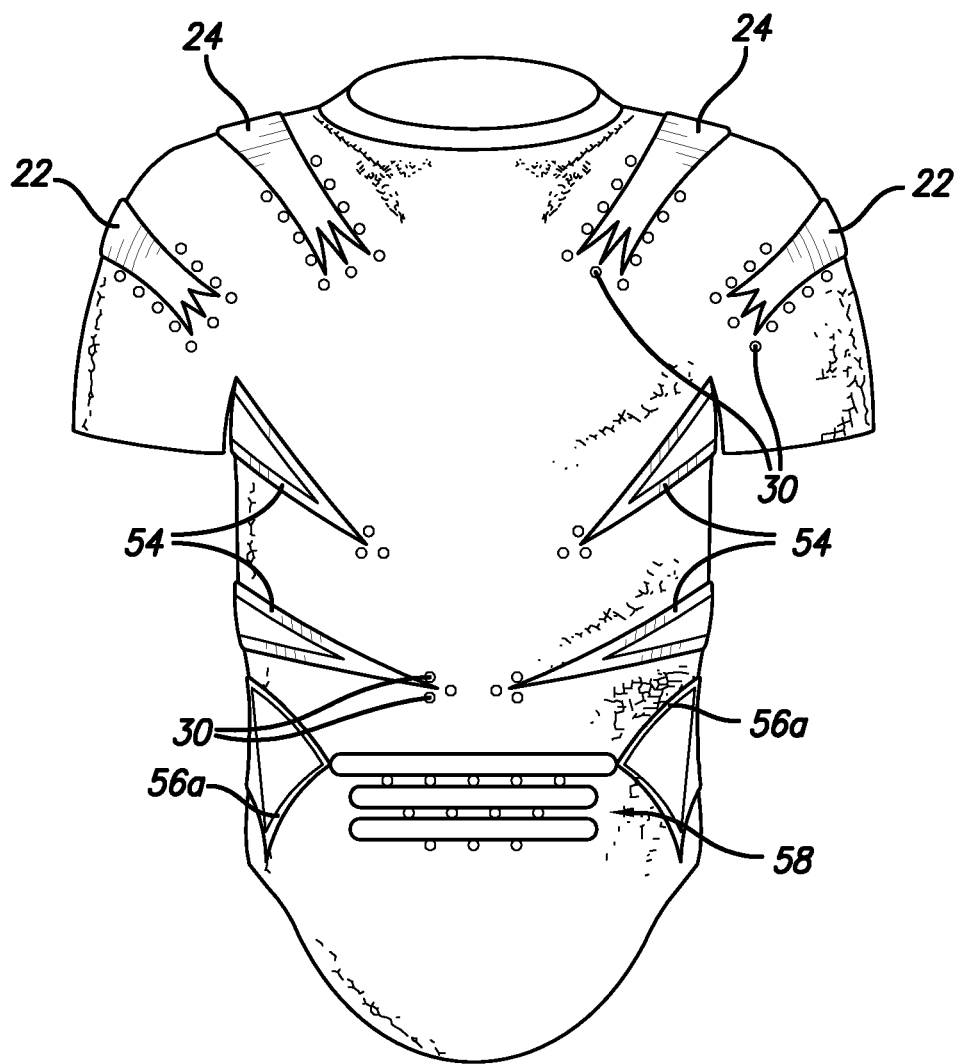
FIG. 13 is a front elevational view of a variation of the garment of FIG. 9 shown inside out to show the features on the inside of the garment.

As shown in FIG. 10, the garment 50 preferably includes at least one upper arm strap 22, at least one shoulder strap 24 and at least one serratus strap 54. These straps 22, 24 and 54 are similar to those described above. In a preferred embodiment, the straps 22, 24 and 54 end in a point that is positioned over a muscle attachment point. For example, the shoulder strap 24 end point is located over the pectoralis minor and the upper arm strap 22 is located over the infra spinitas teres minor. In a preferred embodiment, the ends of the serratus straps 54 are located over the end of the rib cage. The upper serratus strap 54 is positioned over the serratus attachment and the lower strap 54 is positioned over the inter costal. As shown in FIG. 13, in another embodiment of the invention, the straps 22 and 24 (or any of the other straps described herein) can also end in multiple points or tentacles.

The straps 22, 24 and 54 are placed on the inside surface of main body portion 52 so the straps 22, 24 and 54 make direct contact with the nerve receptors in the skin. As described above, the shoulder straps 24 contact the skin over and below the corocoid process of the scapula (muscle attachment of pectoralis minor and short head of biceps and are saturated with acupuncture points) and traction the skin, superior and posteriorly causing the muscles that are attached to the corocoid process to lengthen and open while simulataneously causing a natural reflex called reciprocal inhibition to occur instantly. In use, this causes the opposing muscles to posteriorly tilt the scapula back into its natural position, which increases the joint space. Also, the muscles that extend the neck, upper and mid-spine, contract, tone and optimize the natural linear S-curve of the spine which decreases the common "head carried forward, slumping, failed posture" that often causes pain and disease in humans.

As shown in FIG. 10, the upper arm straps 24 are preferably adjacent the rotator cuff and stimulate external rotation of the humerus within the glenoid cavity. They also stimulate contraction of the horizontal scapular stabilizing muscles. Most shoulders are prone to internal rotation and lack tone in the muscles that resist rolling the shoulders internally. By placing the upper arm straps 24 on the weakened muscle, the strap 24 causes the muscle to contract and tone and support. In use, this helps align the humerus within the glenoid and improves muscle strength, range of motion, proprioception and therefore, function of the shoulder joints.

As shown in FIGS. 10-14, the shirt 50 also includes diamond shaped plate 56. In a preferred embodiment, plate 56 has a front portion 56a that is outlined and a rear portion 56b that is solid. Outlined means that a portion of the plate is cut out, thereby creating a narrow band of material that borders or outlines the diamond shape. As can be seen in FIG. 11, a triangle is defined in the front portion 56a of the plate 56 by the narrow band of material. This is not a limitation on the present invention. In another embodiment, the entire plate 56 can be solid or the entire plate 56 can be outlined. It will be understood that any of the proprioceptive or sensory motor stimulation members (including, but not limited to straps 22, 24 and 54, bands 58, 62 and 64, patches 60, plates 56, neuro nubs 30) can be either solid or outlined. See, for example, FIG. 13, which shows the serratus straps 54 in outlined form. It will be understood that outlined sensory motor stimulation members provide for more motion and encourage movement and solid sensory motor stimulation members encourage stability and compression and activate muscle tone.

It will be understood that each plate 56 (on the left and the right sides of the shirt) extend over the transverse abdominus and the internal oblique muscles, both of which play a key role in core stability.

The shirt 50 also preferably includes at least one and preferably a plurality of lower ab bands 58. As shown in FIG. 10, the ab bands 58 are solid. However, in another embodiment, they can be outlined. The bands 58 are positioned over the lower abs or the lower rectus abdominus and just below umbilicus. In use, the bands 58 cue the lower abs to contract, which results in a reflex action that relaxes the normally hypertoned hip flexors (part of the lower crossed syndrome) and the muscles of the lower back. This helps place the lumbosacral spine in optimal alignment and engages the core (hips, pelvis, and lumbosacral spine) to function optimally.

Figure 14:
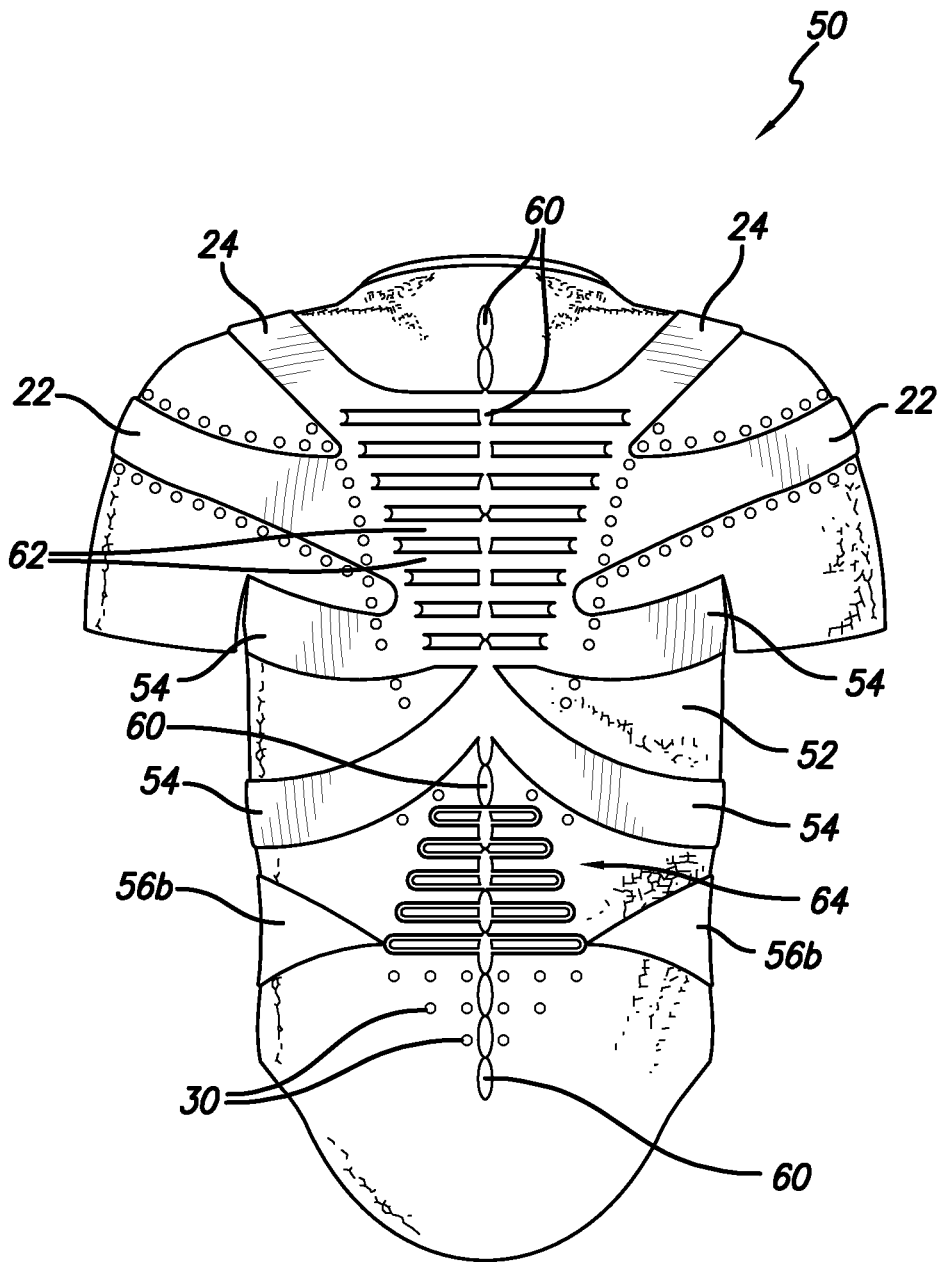
FIG. 14 is a rear elevational view of a variation of the garment of FIG. 9 shown inside out to show the features on the inside of the garment.

As shown in FIG. 12, in a preferred embodiment, the shirt 50 includes a plurality of vertebra patches 60. The patches 60 are preferably positioned over each individual vertebrae in the thoracic and lumbar spine and are interconnected to each other. In another embodiment, the patches may only be positioned over selected vertebrae in the thoracic and/or lumbar spine. In yet another embodiment patches can be positioned over the vertebrae in the cervical spine and/or the lumbar/ lumbo sacral spine. As shown in FIG. 14, in another embodiment, the patches 60 can also be connected to the scapular bands 62 (described below). In use, the patches 60 assist in extension of the thoracic spine and integrate coupled movement by cueing tone to enhance the function of the extensor muscles to provide stability and normal movement patterns to the joints of the cervical and thoracic spine along with the right and left scapulothoracic joints. In other words, the patches in the garment that is positioned over the thoracic vertebra prevents the normal stretch of the skin when the head drops forward. This is what stimulates the cutaneous nerve receptors to cause the muscles to respond appropriately.

As is best shown in FIG. 12, the shirt 50 also includes at least one and preferably a plurality of scapular bands 62. The scapular bands 62 extend over the inter scapular muscles (middle trapezious, lower trapezious, rhomboids major and rhomboids minor) to provide constant cue to these muscles to assist in keeping scapulae in ideal natural movement planes during static and dynamic movement activities.

As is best shown in FIG. 12, the shirt 50 also includes at least one and preferably a plurality of lumbar spine bands 64 for proprioceptive awareness of muscle tone and alignment of the lumbar spine and specific compression of the lumbar spine structures. The lumbar spine bands 64, which are preferably outlined (but can be solid), together with the lower ab bands 58, which are preferably solid, links the abdominal section of core muscles together providing sensory motor feedback for alignment support and function.

The shirt 50 can also include neuro nubs 30, as described above. The neuro nubs 30 are preferably placed in specific areas with richly innervated tissues that correspond to specific acupuncture points to help stimulate circulation, energy and "chi" through areas prone to tension, over use and dysfunction. The nubs 30 also assist in decreasing migration of the garment as the wearer moves freely through all normal range of movements.

As can best be seen in FIGS. 11 and 12, many of the sensory motor stimulation members (e.g., straps 22, 24 and 54) extend in a spiral or helical manner about the axis of the shirt. This causes the skin, muscle and/or tissue under the straps 22, 24 and 54 to be moved or stimulated in a spiral direction when worn. As is described above in the Summary section, this spiral movement is physiologically beneficial. The spiral or helix may extend at any angle. As discussed above, the Fibonacci numbers, hence the helix/spiral shape is important in nature (e.g., the human body) for the smooth flow of energy and enhances human physiology and function. As is shown in FIGS. 10-15, in keeping with the spiral/helical concept, in a preferred embodiment, straps 22, 24 and 54 all generally extend toward or point toward the wearer's opposite hip. In other words, if all of the right straps 22, 24 and 54 were continued downwardly, they would meet at the left hip of the wearer. And, if all of the left straps 22, 24 and 54 were continued downwardly, they would meet at the right hip of the wearer. This is preferable for the portions of the straps 22, 24 and 54 on the back and front of the shirt. This is not a limitation on the invention. In other embodiments, the straps can extend at different angles. This orientation of the straps 22, 24 and 54 is in accordance with nature's rules of alignment and energy flow (i.e., the Fibonacci Numbering System discussed above). This helps achieve anatomical alignment with improved and more focal stimulation using the body's natural diagonal and spiral angles of alignment and movement. This angle of orientation along with other features, such as the lower abdominal toning cue (via lower ab bands 58); the anatomically specific thoraco-lumbo-sacral support (via vertebra patches 60 and lumbar bands 64) stimulates thoracic spinal extensor muscles and provides proprioceptive feedback to the T-L-S spine. The addition of the transverse abdominis and the internal oblique plate 56 stimulates these important core stabilizing muscles.... "Outlined" horizontal bands 64 add specific, moderate compression throughout the lumbar spine and upper core by preferably connecting/linking to the transverse abdominis and internal oblique muscle plates 56 which preferably connects/links to the "solid" horizontal lower abdominal bands 58.

It will be understood that in manufacturing the garment 50, the various sensory motor stimulation members can be separate pieces of material or can be interconnected or a single piece. For example, FIG. 12 shows that the patches 60, scapular bands 62 and straps 22, 24 and 54 are all separate pieces of material. However, FIG. 14 shows that they are all a single piece of material.

Essentially, the garment of the invention functions to create an exoskeleton for the user's body, thereby allowing for the sensory motor stimulation for proprioceptive awareness and treatment of strategic regions. Increased pressure is applied to these strategic body regions to perform the advantageous proprioceptive treatment. Prior art approaches involved mechanical treatment, i.e. physically manipulating portions of the body to desired configurations. This modern inventive approach instead induces a nervous system response, which responds to stimuli at the speed of light, through the application of strategic proprioceptive compression. There is no attempt to physically move large portions of the body. Instead, the garment does not move the wearer, it stimulates the sensory motor system to cause the muscles to do it naturally.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A garment adapted to be worn by a wearer, the garment comprising:
    an outer layer configured to be worn over at least a portion of a wearer's torso, wherein the outer layer has an anterior portion, a posterior portion, an inner surface and an outer surface, and a neck region and a waist region; and
    at least one sensory motor stimulation member disposed at the inner surface of the outer layer, wherein, when the garment is worn by the wearer the at least one sensory motor stimulation member contacts a portion of a wearer's skin, and, when the wearer moves the at least one sensory motor stimulation member alters a normal stretch of a portion of the skin contacted by the at least one sensory motor stimulation member, thereby stimulating wearer's cutaneous nerve receptors to cause wearer's muscles to respond appropriately, wherein the at least one sensory motor stimulation member comprises:
    vertebra patches extending longitudinally along the posterior portion from a center of the posterior portion towards the neck region and from the center of the posterior portion towards the waist region; and
    two serratus straps each extending from the vertebra patches towards the anterior portion, wherein, when the garment is worn by the wearer, an end of each serratus strap is configured to be located over a serratus muscle attachment point of the wearer.

2. The garment of claim 1, wherein the at least one sensory motor stimulation member further comprises left and right shoulder straps extending from the vertebra patches.

3. The garment of claim 2, wherein each of the left and right shoulder straps is configured to contact the wearer's skin over a coracoid process of the scapula.

4. The garment of claim 3, wherein the left and right shoulder straps each include a front end on the anterior portion, and wherein the garment further comprises at least one neuro nub adjacent to the front end of each of the left and right shoulder straps.

5. The garment of claim 1, wherein the posterior portion has an inner surface and an outer surface, and the at least one sensory motor stimulation member further comprises a plurality of generally horizontally extending scapular bands disposed at the inner surface of the posterior portion, wherein the plurality of generally horizontally extending scapular bands are made of a single piece of material.

6. The garment of claim 1, wherein the posterior portion has an inner surface and an outer surface, and the at least one sensory motor stimulation member further comprises the vertebra patches disposed at the inner surface of the posterior portion, wherein the vertebra patches are configured to be positioned over multiple thoracic vertebrae of the wearer when worn by the wearer and configured to prevent a normal stretch of a skin of the wearer along the multiple thoracic vertebrae of the wearer.

7. The garment of claim 1, wherein the two serratus straps comprise left and right upper serratus straps extending from the vertebra patches.

8. The garment of claim 1, wherein the anterior portion has an inner surface and an outer surface, the at least one sensory motor stimulation member further comprises a plurality of lower ab bands disposed at the inner surface of the anterior portion, and the plurality of lower ab bands is fabricated of an elastomeric material.

9. The garment of claim 1, wherein the posterior portion has an inner surface and an outer surface, and the at least one sensory motor stimulation member further comprises a plurality of lumbar spine bands disposed at the inner surface of the posterior portion.

10. The garment of claim 1, wherein the at least one sensory motor stimulation member further comprises left and right upper arm straps.

11. The garment of claim 1, wherein the at least one sensory motor stimulation member further comprises a shoulder strap, upper arm strap, diamond shaped plate, lower ab band, scapular band and lumbar spine band.

12. The garment of claim 1, wherein the garment defines a generally vertically extending axis, and at least one sensory motor stimulation member is positioned such that it extends in a spiral about the generally vertically extending axis defined by the garment.

13. The garment of claim 1, further comprising two diamond shaped plates, wherein each diamond shaped plate includes a front portion and a rear portion, the front portion defining a triangular cut out.

14. The garment of claim 1, wherein the at least one sensory motor stimulation member includes two shoulder straps and two upper arm straps, each of which end in multiple points.

15. A method comprising the steps of:
    donning a garment that covers at least a portion of a wearer's torso, wherein the garment includes a main body portion and at least one sensory motor stimulation member associated with the main body portion, wherein the garment is form-fitting, and the main body portion includes an anterior portion and a posterior portion that includes a neck region and a waist region, wherein the at least one sensory motor stimulation member is configured to contact a portion of a wearer's skin and the at least one sensory motor stimulation member comprises:
        vertebra patches extending longitudinally along the posterior portion from a center of the posterior portion towards the neck region and from the center of the posterior portion towards the waist region; and
        two serratus straps each extending from the vertebra patches towards the anterior portion, wherein, when the garment is worn by a wearer, an end of each serratus strap is configured to be located over a serratus muscle attachment point of the wearer;
    moving while wearing the garment; and
    stimulating cutaneous nerve receptors in a portion of the wearer's skin contacted by the at least one sensory motor stimulation member.

16. The method of claim 15, wherein the main body portion includes an outer surface and an inner surface, and at least one sensory motor stimulation member is disposed at the inner surface of the main body portion.

17. The method of claim 15, wherein the at least one sensory motor stimulation member comprises a shoulder strap, upper arm strap, diamond shaped plate, lower ab band, scapular band and lumbar spine band.

18. The method of claim 15, further comprising the step of removing and donning the garment a plurality of times over a period of time, wherein at the end of the period of time agonist and antagonist muscles positioned under at least one sensory motor stimulation member are in positions that are more balanced than at the beginning of the period of time.

* * * * *